(12) United States Patent
Quintini et al.

(10) Patent No.: US 11,594,324 B2
(45) Date of Patent: Feb. 28, 2023

(54) SYSTEM AND METHOD FOR MONITORING SURGICAL OBJECTS

(71) Applicant: THE CLEVELAND CLINIC FOUNDATION, Cleveland, OH (US)

(72) Inventors: Cristiano Quintini, Cleveland, OH (US); Douglas R. Johnston, Cleveland, OH (US); Edward Soltesz, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 895 days.

(21) Appl. No.: 16/477,211

(22) PCT Filed: Jan. 11, 2018

(86) PCT No.: PCT/US2018/013254
§ 371 (c)(1),
(2) Date: Jul. 11, 2019

(87) PCT Pub. No.: WO2018/132527
PCT Pub. Date: Jul. 19, 2018

(65) Prior Publication Data
US 2019/0362839 A1 Nov. 28, 2019

Related U.S. Application Data

(60) Provisional application No. 62/445,450, filed on Jan. 12, 2017.

(51) Int. Cl.
*G16H 40/20* (2018.01)
*G06V 20/52* (2022.01)
(Continued)

(52) U.S. Cl.
CPC .......... *G16H 40/20* (2018.01); *G06F 16/538* (2019.01); *G06F 16/5854* (2019.01);
(Continued)

(58) Field of Classification Search
CPC .......... G06T 2207/30242; G06V 20/52; A61B 2090/0805; G16H 40/20
See application file for complete search history.

(56) References Cited

U.S. PATENT DOCUMENTS 4,943,939 A * 7/1990 Hoover .................. A61B 50/36
221/92
5,629,498 A * 5/1997 Pollock .................. G01G 17/04
177/244

(Continued)

FOREIGN PATENT DOCUMENTS

CA            2276837 A1 *  1/2000
WO     WO-2017035474 A1 *  3/2017

OTHER PUBLICATIONS

N. Rivera et al., "ASSIST—Automated System for Surgical Instrument and Sponge Tracking," 2008 IEEE International Conference on RFID, 2008, pp. 297-302, doi: 10.1109/RFID.2008.4519358. (Year: 2008).*

(Continued)

*Primary Examiner* — Michael Robert Cammarata
(74) *Attorney, Agent, or Firm* — Tarolli, Sundheim, Covell & Tummino LLP

(57) ABSTRACT

A system for monitoring surgical objects is provided. An entry scanner captures a first set of image data from a surgical object identifier. A containment surface defines a target field of view. An exit scanner captures a second set of image data from a surgical object identifier within the target field of view. A monitoring system is electrically connected to at least one of the entry and exit scanners. The monitoring system has a surgical object recognition module having a database of pre-existing surgical object identifier data. The surgical recognition module identifies at least one of the number of surgical objects, the type of surgical objects, and the number of each type of surgical objects from the first and (Continued)

second sets of image data by comparing the first and second sets of image data with the pre-existing surgical object identifier data.

18 Claims, 5 Drawing Sheets

(51) Int. Cl.
| | |
|---|---|
| A61B 90/00 | (2016.01) |
| G16H 30/20 | (2018.01) |
| G06F 16/583 | (2019.01) |
| G06F 16/538 | (2019.01) |
| G06V 10/75 | (2022.01) |
| G06V 30/142 | (2022.01) |
| G06Q 10/08 | (2012.01) |
| G06T 7/60 | (2017.01) |
| G06Q 10/087 | (2023.01) |

(52) U.S. Cl.
CPC ............ *G06Q 10/087* (2013.01); *G06T 7/60* (2013.01); *G06V 10/751* (2022.01); *G06V 20/52* (2022.01); *G06V 30/142* (2022.01); *G16H 30/20* (2018.01); *A61B 2090/0805* (2016.02); *G06T 2207/30242* (2013.01)

(56) References Cited

U.S. PATENT DOCUMENTS

| | | | | |
|---|---|---|---|---|
| 6,223,137 | B1* | 4/2001 | McCay | G09B 23/28 |
| | | | | 235/375 |
| 7,180,014 | B2* | 2/2007 | Farber | G16H 40/20 |
| | | | | 606/1 |
| 9,168,104 | B2* | 10/2015 | Dein | A61B 34/20 |
| 11,367,184 | B2* | 6/2022 | Tosun | G06T 7/0012 |
| 2007/0083170 | A1* | 4/2007 | Stewart | G06Q 10/30 |
| | | | | 604/358 |
| 2008/0237341 | A1* | 10/2008 | Fleck | G06K 7/01 |
| | | | | 235/385 |
| 2009/0317002 | A1* | 12/2009 | Dein | A61B 90/90 |
| | | | | 340/568.1 |
| 2015/0168207 | A1* | 6/2015 | Pollock | G01G 21/28 |
| | | | | 177/1 |
| 2015/0302157 | A1* | 10/2015 | Collar | A61B 50/10 |
| | | | | 382/128 |
| 2016/0371574 | A1* | 12/2016 | Nguyen | G06K 17/0022 |
| 2018/0338801 | A1* | 11/2018 | Barnett | A61B 34/25 |
| 2018/0353256 | A1* | 12/2018 | Stewart | G16H 40/40 |
| 2022/0181020 | A1* | 6/2022 | Keshavjee | G06F 3/013 |

OTHER PUBLICATIONS

J. Tan, S. Wang, H. Wang and J. Zheng, "A new method of surgical instruments automatic identification and counting," 2011 4th International Congress on Image and Signal Processing, 2011, pp. 1797-1800, doi: 10.1109/CISP.2011.6100602. (Year: 2011).*

D. Bouget, R. Benenson, M. Omran, L. Riffaud, B. Schiele and P. Jannin, "Detecting Surgical Tools by Modelling Local Appearance and Global Shape," in IEEE Transactions on Medical Imaging, vol. 34, No. 12, pp. 2603-2617, Dec. 2015, doi: 10.1109/TMI.2015.2450831. (Year: 2015).*

E. Hanada, A. Ohira, M. Hayashi and T. Sawa, "Improving efficiency through analysis of data obtained from an RFID tag system for surgical instruments," 2015 IEEE 5th International Conference on Consumer Electronics—Berlin (ICCE—Berlin), 2015, pp. 84-87, doi: 10.1109/ICCE-Berlin.2015.7391339. (Year: 2015).*

Y. Xu et al., "Robotic Handling of Surgical Instruments in a Cluttered Tray," in IEEE Transactions on Automation Science and Engineering, vol. 12, No. 2, pp. 775-780, Apr. 2015, doi: 10.1109/TASE.2015.2396041. (Year: 2015).*

* cited by examiner

SYSTEM AND METHOD FOR MONITORING SURGICAL OBJECTS

CROSS-REFERENCE TO RELATED APPLICATIONS

This application is a National Phase filing of PCT/US2018/013254, filed 11 Jan. 2018, which claims priority from U.S. Provisional Application No. 62/445,450, filed 12 Jan. 2017. Each of the above-identified applications are incorporated herein by reference in their entireties for all purposes.

TECHNICAL FIELD

This disclosure relates to a system and method for monitoring surgical objects.

BACKGROUND

Over the course of a medical procedure, a large number of surgical objects such as needles, sponges, and medical instruments may be used in an operating environment. All surgical objects should be accounted for at the conclusion of surgery.

SUMMARY

In an aspect, a system for monitoring surgical objects is provided. An entry scanner captures a first set of image data from a surgical object identifier. A containment surface defines a target field of view. An exit scanner captures a second set of image data from a surgical object identifier within the target field of view on. A monitoring system is electrically connected to at least one of the entry scanner and the exit scanner. The monitoring system has a surgical object recognition module. The surgical object recognition module has a processor and a database of pre-existing surgical object identifier data. The surgical object recognition module identifies at least one of the number of surgical objects, the type of surgical objects, and the number of each type of surgical objects from the first set of image data by comparing the first set of image data with the pre-existing surgical object identifier data to produce at least one of a surgical object entry count and a surgical object type entry count. The surgical object recognition module identifies at least one of the number of surgical objects, the type of surgical objects, and the number of each type of surgical objects from the second set of image data by comparing the second set of image data with the pre-existing surgical object identifier data to produce at least one of a surgical object exit count and a surgical object exit type count. The surgical object entry count is a numerical representation of the number of surgical objects identified by the monitoring system from the first set of image data. The surgical object type entry count is a separate numerical representation of the number of each separate type of surgical objects identified by the monitoring system from the first set of image data. The surgical object exit count is a numerical representation of the number of surgical objects identified by the monitoring system from the second set of image data. The surgical object type exit count is a separate numerical representation of the number of each separate type of surgical objects identified by the monitoring system from the second set of image data. A display screen is electrically connected to the monitoring system. The display screen displaying, in a user-perceptible format, at least one of the surgical object entry count, the surgical object exit count, the surgical object type entry count, the surgical object type exit count, the difference between the surgical object entry count and the surgical object exit count, and the difference between the surgical object type entry count and the surgical object type exit count.

In an aspect, a method for monitoring surgical objects is provided. A system for monitoring surgical objects is provided. The system for monitoring surgical objects has an entry scanner that captures a first set of image data from a surgical object identifier. A containment surface is at least one of magnetic and adhesive-provided to selectively restrict at least one surgical object to the containment surface. An exit scanner captures a second set of image data from a surgical object identifier within a target field of view on the containment surface. A monitoring system is electrically connected to at least one of the entry scanner and the exit scanner. The monitoring system has a surgical object recognition module. The surgical object recognition module has a processor and a database of pre-existing surgical object identifier data. The surgical object recognition module identifies at least one of the number of surgical objects, the type of surgical objects, and the number of each type of surgical objects from at least one of the first set of image data and the second set of image data. A display screen is electrically connected to the monitoring system. A first set of image data is captured from a surgical object identifier with the entry scanner. The first set of image data is electrically transferred from the entry scanner to the monitoring system. The database of pre-existing surgical object identifier data is queried to match the first set of image data to the pre-existing surgical object identifier data to produce at least one of a surgical object entry count and a surgical object type entry count. The surgical object entry count being a numerical representation of the number of surgical objects identified by the monitoring system from the first set of image data. The surgical object type entry count is a separate numerical representation of the number of each separate type of surgical objects identified by the monitoring system from the first set of image data. At least one of the surgical object entry count and the surgical object type entry count is electrically transferred from the monitoring system to the display screen. At least one of the surgical object entry count and the surgical object type entry count is displayed in a user-perceptible manner. The surgical object is placed and selectively restricted on the containment surface by utilizing at least one of magnetic and adhesive properties of the containment surface. With the surgical object on the containment surface, a second set of image data is captured from the surgical object identifier with the exit scanner. The second set of image data is electrically transferred from the exit scanner to the monitoring system. The database of pre-existing surgical object identifier data is queried to match the second set of image data to the pre-existing surgical object identifier data to produce at least one of a surgical object exit count and a surgical object type exit count. The surgical object exit count is a numerical representation of the number of surgical objects identified by the monitoring system from the second set of image data. The surgical object type exit count is a separate numerical representation of the number of each separate type of surgical objects identified by the monitoring system from the second set of image data. At least one of the surgical object exit count and the surgical object type exit count is electrically transferred from the monitoring system to the display screen. At least one of the surgical object exit count and the surgical object type exit count is displayed in a user-perceptible manner. At least one of the displayed surgical object entry count and the displayed surgical object type entry count is compared to at least one of the displayed surgical object exit count and the displayed surgical object type exit count.

BRIEF DESCRIPTION OF THE DRAWINGS

For a better understanding, reference may be made to the accompanying drawings, in which.

DESCRIPTION OF EMBODIMENTS

Unless defined otherwise, all technical and scientific terms used herein have the same meaning as is commonly understood by one of skill in the art to which the present disclosure pertains.

As used herein, the term "user" can be used interchangeably to refer to an individual who prepares for, assists, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

It will be understood that when an element is referred to as being "on," "attached" to, "connected" to, etc., another element, it can be directly on, attached to or connected to the other element or intervening elements may also be present.

Spatially relative terms, such as "below," "lower," "over" and the like, may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures. For example, if a device in the Figures is inverted, elements described as "under" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 1:
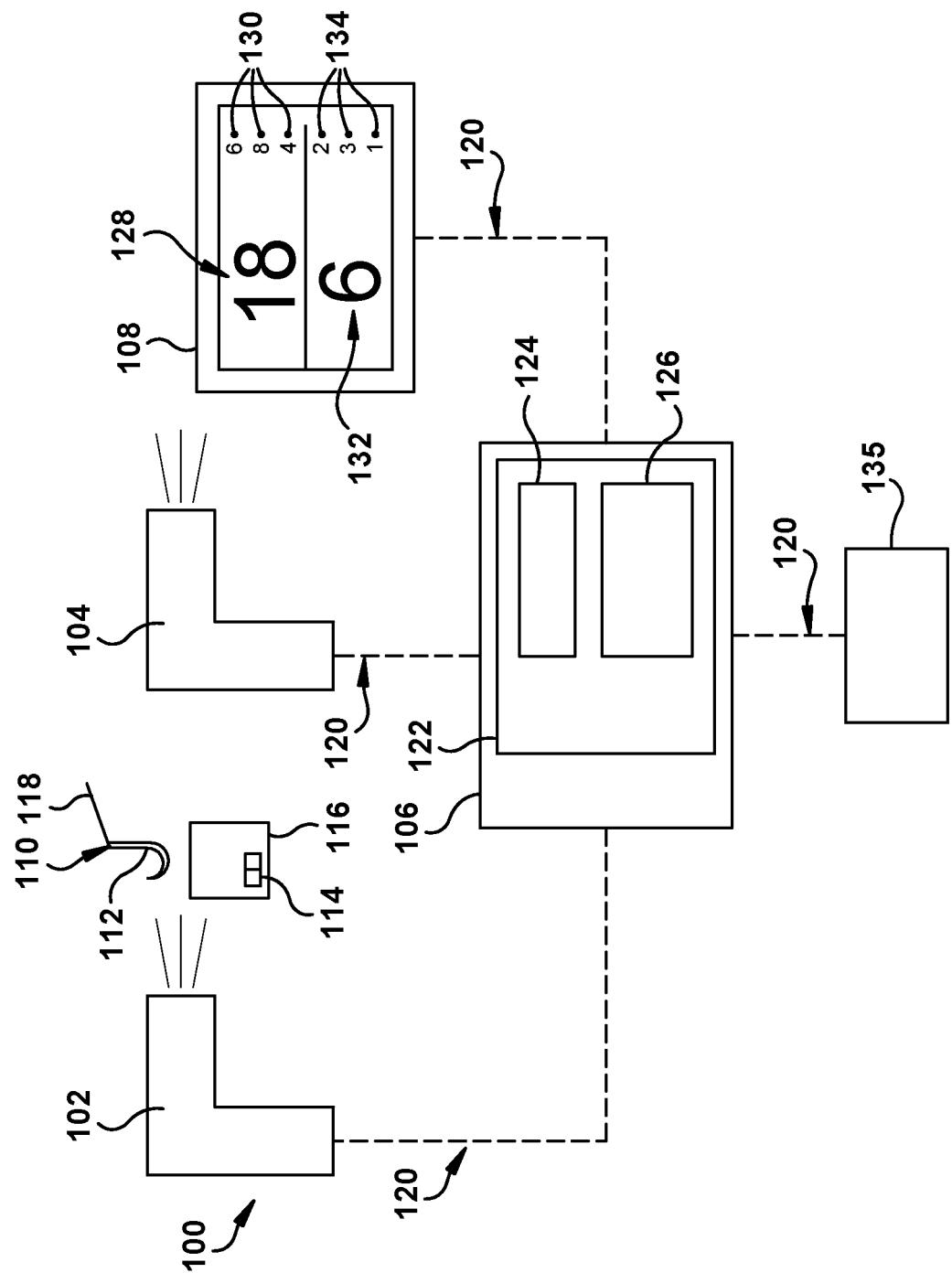
FIG. 1 is a schematic view of a system for monitoring surgical objects according to one aspect of the present invention.

FIG. 1 depicts a system for monitoring, such as by counting and discarding, surgical objects 100. The system for monitoring surgical objects 100 includes an entry scanner 102, an exit scanner 104, a monitoring system 106, and a display screen 108. The entry scanner 102 captures a first set of image data from a surgical object identifier 110. The exit scanner 104 captures a second set of image data from a surgical object identifier 110. At least one of the entry scanner and exit scanner may be a handheld device. The entry and exit scanners 102, 104 may be configured to capture the first and second set of image data, respectively, at any desirable location, such as, but not limited to, on any table in any operating environment, on any other table in any other environment, on a surgical tray, at bedside, in a storage room, at any other desirable location, or any combination thereof.

The surgical object identifier 110 may be at least one physical characteristic of a surgical object 112. The surgical object 112 may be one or more of a suture needle, a surgical sponge, a surgical instrument, any other surgical object that is inventoried within the operating room by the staff, or any combination thereof. The physical characteristic may be at least one of the shape of the surgical object 112, the size of the surgical object 112, the weight of the surgical object 112, the color of the surgical object 112, the outline (e.g., silhouette or footprint) of the surgical object 112, any other tangible identifier on the surgical object 112, or any combination thereof. The surgical object identifier 110 may be a label 114 on a surgical object package 116 readable by at least one of the entry and exit scanners 102, 104. The label 114 may contain data pertaining to at least one of the total number of surgical objects 112 within the surgical object package 116, the types of each surgical object 112 within the surgical object package 116, and the number of each type of surgical objects 112 within the surgical object package 116. The label 114 may be at least one of a UPC barcode, an RFID tag, an EAN barcode, any other barcode, a QR code, any alpha-numeric-based label, or any other scanner-perceptible marking. The surgical object 112 may have an attached discardable material 118. The discardable material 118 may be excess suture threading or any other appropriate material that is attached to a surgical object 112 and discarded at any desired time during and/or after a medical procedure.

The monitoring system 106 is electrically connected 120 to at least one of the entry scanner 102 and the exit scanner 104 for power and/or communication purposes. The electrical connection 120 may be a wired and/or wireless connection. The monitoring system 106 has a surgical object recognition module 122. The surgical object recognition module 122 has a processor 124 and a database of pre-existing surgical object identifier data 126. The surgical object recognition module 122 may identify at least one of the number of surgical objects 112, the type of surgical objects 112, and the number of each type of surgical objects 112 from the first set of image data by comparing the first set of image data with the pre-existing surgical object identifier data to produce at least one of a surgical object entry count 128 and a surgical object type entry count 130. The surgical object entry count 128 is a numerical representation of the number of surgical objects 112 identified by the monitoring system 106 from the first set of image data. The surgical object type entry count 130 is a separate numerical representation of the number of each separate type of surgical objects 112 identified by the monitoring system 106 from the first set of image data.

The surgical object recognition module 122 may identify at least one of the number of surgical objects 112, the type of surgical objects 112, and the number of each type of surgical objects 112 from the second set of image data by comparing the second set of image data with the pre-existing surgical object identifier data to produce at least one of a surgical object exit count 132 and a surgical object type exit count 134. The surgical object exit count 132 is a numerical representation of the number of surgical objects 112 identified by the monitoring system 106 from the second set of image data. The surgical object type exit count 134 is a separate numerical representation of the number of each separate type of surgical objects 112 identified by the monitoring system 106 from the second set of image data.

The display screen 108 is electrically connected 120 to the monitoring system 106 for power and/or communication purposes. The display screen 108 may display, in a user-perceptible format, at least one of the surgical object entry count 128, the surgical object exit count 132, the surgical object type entry count 130, the surgical object type exit count 134, the difference between the surgical object entry count 128 and the surgical object exit count 132, and the difference between the surgical object type entry count 130 and the surgical object type exit count 134. The display screen 108 may function as a digital log sheet by displaying, in a user-perceptible format, at least one of the surgical object entry count 128, the surgical object exit count 132, the surgical object type entry count 130, the surgical object type exit count 134, the difference between the surgical object entry count 128 and the surgical object exit count 132, and the difference between the surgical object type entry count 130 and the surgical object type exit count 134. The user-perceptible format may be at least one of auditory, tactile, and visual.

The monitoring system 106 may be electrically connected 120 to at least one external system 135. The external system 135 may be at least one of a billing system, a patient record system, a digital log system, a data storage system, a quality improvement system, or any other appropriate medical system. The monitoring system 106 may electrically transfer at least one of the first set of image data, the second set of image data, the surgical object entry count 128, the surgical object exit count 132, the surgical object type entry count 130, the surgical object type exit count 134, the difference between the surgical object entry count 128 and the surgical object exit count 132, and the difference between the surgical object type entry count 130 and the surgical object type exit count 134 to the at least one external system 135 to compile an accurate bill, provide accurate patient records, be stored in a data storage system, be used in a quality improvement system, provide accurate digital logs of surgical objects 112 identified by the monitoring system 106 from at least one of the first and second sets of image data, and/or to be used in any other external system process or for any other reason.

For example, the monitoring system 106 may electrically transfer at least one of the first set of image data, the second set of image data, the surgical object entry count 128, the surgical object exit count 132, the surgical object type entry count 130, the surgical object type exit count 134, the difference between the surgical object entry count 128 and the surgical object exit count 132, and the difference between the surgical object type entry count 130 and the surgical object type exit count 134 to a medical record system in order to be stored as a portion of a patient's medical record. Prior to being electrically transferred to at least one external system 135, at least one of the first set of image data, the second set of image data, the surgical object entry count 128, the surgical object exit count 132, the surgical object type entry count 130, the surgical object type exit count 134, the difference between the surgical object entry count 128 and the surgical object exit count 132, and the difference between the surgical object type entry count 130 and the surgical object type exit count 134 may be converted by the monitoring system 106 into a standardized file format and/or any other desired file format.

Figure 2:
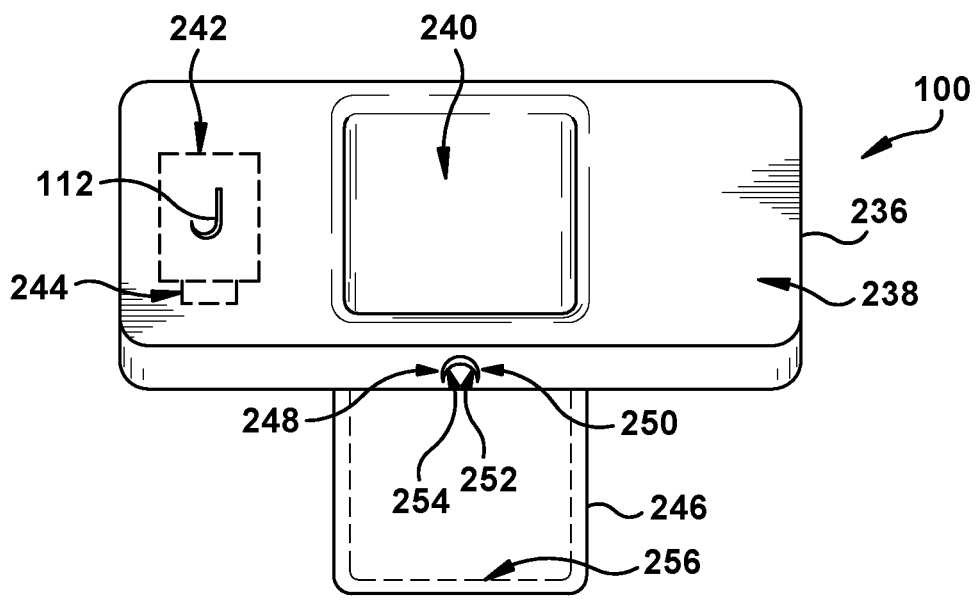
FIG. 2 is a top view of an element of the aspect of FIG. 1.

As shown in FIG. 2, the system for monitoring surgical objects 100 may include a containment member 236. The containment member 236 has containment surface 238 and a disposal recess 240. The containment surface 238 defines a target field of view. At least a portion of the containment surface 238 may be at least one of magnetic and adhesive-provided. A containment surface 238 that is at least partially magnetic may at least partially selectively restrict a surgical object 112 on the containment surface 238 by utilizing the magnetic force of the magnets provided in the magnetic containment surface 238 to at least partially selectively prevent the surgical object 112 from egressing from the magnetic containment surface 238. The surgical object 112 may additionally, or instead, be selectively restricted on the containment surface 238 by the properties of an adhesive at least partially provided on the adhesive-provided containment surface 238 at least partially selectively preventing the surgical object 112 from egressing from the adhesive-provided containment surface 238. The exit scanner 104 may capture the second set of image data from the surgical object identifier 110 within the target field of view.

The containment member 236, or any other portion of the system for monitoring surgical objects 100, may have an electromagnet 242 that is capable of being selectively transitioned between an off position and an on position. The electromagnet 242 in the on position produces a magnetic field to selectively restrict at least one surgical object 112 to at least a portion of the containment surface 238 and prevent the at least one surgical object 112 from egressing from the containment surface 238. The electromagnetic 242 in the off position does not produce a magnetic field. When the surgical object 112 is on the containment surface 238, the electromagnet 242 may be moved into the on position to selectively restrict the surgical object 112 to the containment surface 238 by utilizing the magnetic force of the electromagnet 242. When the selective restriction of the surgical object 112 is no longer desired, the electromagnet 242 may be moved to into the off position to remove the magnetic force selectively restricting the surgical object 112. The electromagnet 242 may be positioned longitudinally below at least a portion of the containment surface 238. The term "longitudinal" is used herein to indicate a substantially vertical direction, in the orientation of FIG. 2.

The electromagnet 242, or any other portion of the system for monitoring surgical objects 100, may have a surgical object detection member 244. The surgical object detection member 244 may be located proximately to the containment surface 238. The surgical object detection member 244 is configured to detect when a surgical object 112 is located on at least a portion of the containment surface 238. When the surgical object detection member 244 detects a surgical object 112 on at least a portion of the containment surface 238, the surgical object detection member 244 transitions the electromagnet 242 to the on position. The surgical object detection member 244 may be a motion sensor, optical sensor, a magnetic sensor, a force sensor, a weight detection sensor, any other appropriate detector, or any combination thereof.

The containment member 236 may have a disposal container 246 longitudinally extending downward from the disposal recess 240 and a discardable material cutter 248. The discardable material cutter 248 is configured to cut the discardable material 118 attached to a surgical object 112. The discardable material cutter 248 may be any appropriate mechanical and/or electric device that is capable of cutting and/or detaching the discardable material 118 from the surgical object 112. The discardable material cutter 248 may be, for example, a v-shaped notch 250 having an inner surface 252 with a blade 254 disposed thereon. A user may insert the discardable material 118 into the v-shaped notch 250 and pull the discardable material 118 against the blade 254 to sever the discardable material 118. For example, excess suture thread could be removed from a needle for separate discarding via the discardable material cutter 248. It is contemplated that when the surgical object detection member 244 detects a surgical object 112 on at least a portion of the containment surface 238, the surgical object detection member 244 may actuate the discardable material cutter 248 to cut the discardable material 118 from the surgical object 112. The disposal container 246 may have a lower surface 256 that is magnetic and/or adhesive-provided. The magnetic and/or adhesive properties of the lower surface 256 may be used to selectively restrict surgical objects and/or discardable material 118 to the disposal container 246.

Figure 3:
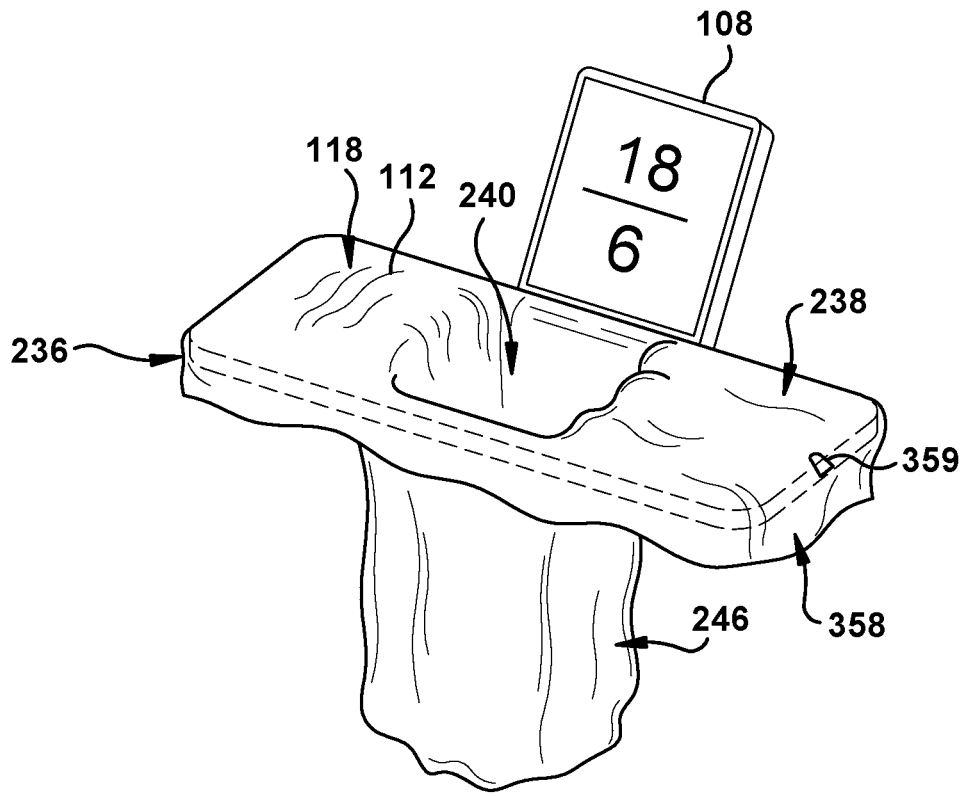
FIG. 3 is a top view of an element of the aspect of FIG. 1.

As shown in FIG. 3, the display screen 108 may be attached to the containment member 236. The containment member 236 may have a selectively removable disposable cover 358. The disposable cover 358 may be configured to selectively and concurrently cover at least a portion of the containment surface 238 and at least a portion of the disposal recess 240. The disposable cover 358 may be configured to cover at least a portion of the disposal container 246. A portion of the disposable cover 358 covering the disposal recess 240 may form the disposal container 246. The disposable cover 358 may be selectively secured to the containment member 236 through the use of a fastener 359. The fastener 359 may be at least one of a clip, an adhesive, a hook and loop fastener, a magnetic fastener, a snap fastener, a hook and eye fastener, a button, a zipper, a string and eye fastener, a saw tooth fastener, or any other suitable fastener or combination of fasteners. The disposable cover 358 may be at least partially magnetic and/or adhesive-provided to selectively restrict at least one surgical object 112 to at least one of the disposable cover 358, the containment surface 238, and the disposal container 246.

Figure 4:
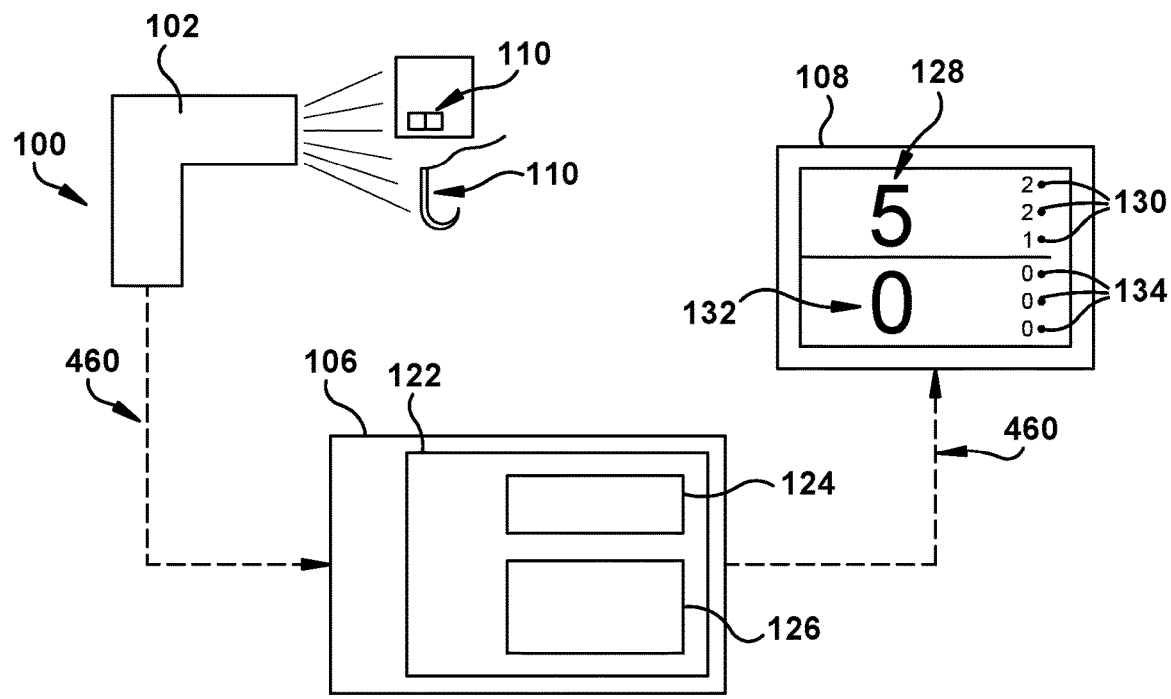
FIGS. 4-5 illustrate an example sequence of operation of a portion of the aspect of FIG. 1.

In use, the system for monitoring surgical objects 100 is provided. As shown in FIG. 4, prior to at least a portion of a medical procedure, a first set of image data is captured from a surgical object identifier 100 with the entry scanner 102. The first set of image data is electrically transferred 460 from the entry scanner 102 to the monitoring system 106. The electric transfer 460 may be a wired and/or wireless transfer. The database of pre-existing surgical object identifier data 126 is queried to match the first set of image data to the pre-existing surgical object identifier data to produce at least one of the surgical object entry count 128 and the surgical object type entry count 130.

At least one of the surgical object entry count 128 and the surgical object type entry count 130 is electrically transferred 460 from the monitoring system 106 to the display screen 108. At least one of the surgical object entry count 128 and the surgical object type entry count 130 is displayed in a user-perceptible manner. The disposable cover 358, when provided, may be concurrently placed on at least a portion of the containment surface 238 and at least a portion of the disposal recess 240.

Figure 5:
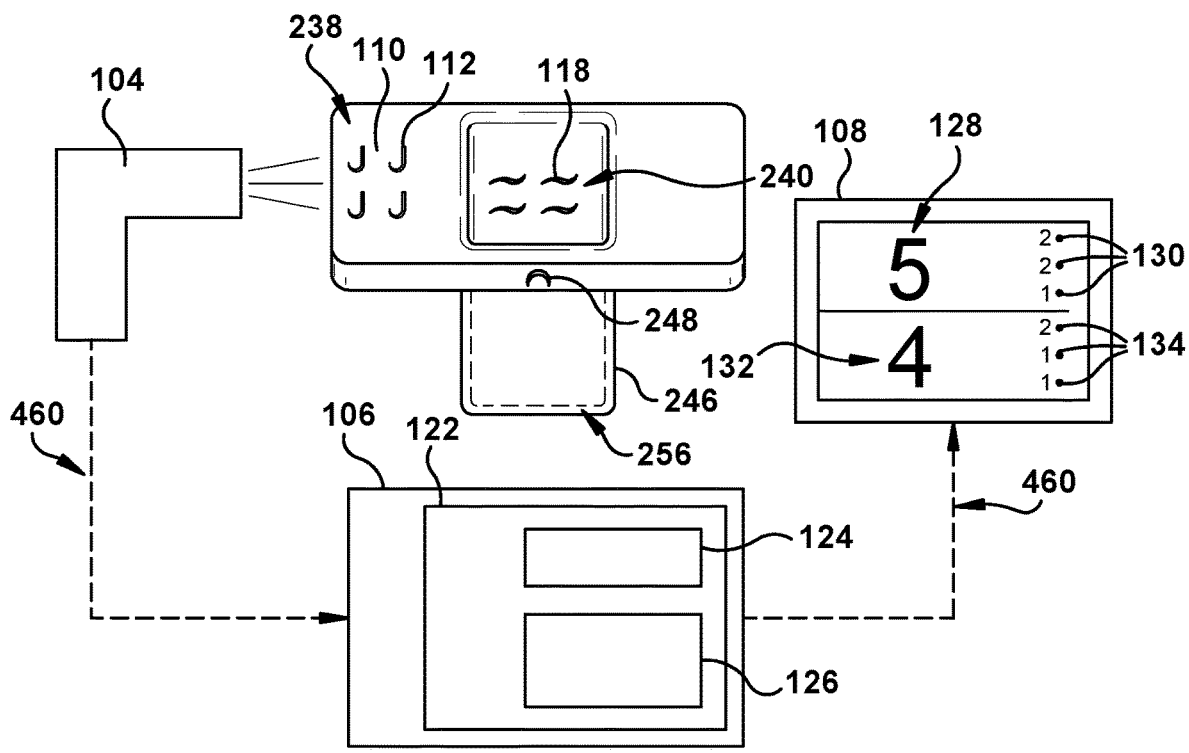

Following and/or during at least a portion of the medical procedure, any discardable material 118 may be detached from the surgical object 112 by cutting the discardable material 118 with the discardable material cutter 248, when provided. As shown in FIG. 5, the surgical object 112 is placed and selectively restricted on the containment surface 238, and on a portion of the disposable cover 358 that is covering the containment surface 238, when provided, by utilizing the magnetic and/or adhesive properties of the containment surface 238 and/or the disposable cover 358. For example, a surgical object 112 may be at least partially selectively restricted on the containment surface 238 by the magnetic force of magnets provided in the magnetic containment surface 238 and/or the magnetic disposable cover at least partially selectively preventing the surgical object 112 from egressing from the magnetic containment surface 238. The surgical object 112 may be at least partially selectively restricted on the containment surface 238 by the properties of an adhesive provided on the adhesive-provided containment surface 238 and/or adhesive-provided disposable cover 358 at least partially selectively preventing the surgical object 112 from egressing from the adhesive-provided containment surface 238. The surgical object 112 may additionally, or instead, be selectively restricted on the containment surface 238 by the magnetic force of the electromagnet 242, when provided, as described above.

Any discardable material 118 is discarded into the disposal recess 240, and onto the portion of the disposable cover 358 that is covering the disposal recess 240, when provided. The discardable material 118 may pass through the disposal recess 240 and into the disposal container 246, when provided. The magnetic and/or adhesive-provided lower surface 256 of the disposal container 246, when provided, may selectively restrict the discardable material 118 from egressing from the disposal container 246.

With the surgical object 112 on the containment surface 238, a second set of image data is captured from the surgical object identifier 110 with the exit scanner 104. The second set of image data is electrically transferred 460 from the exit scanner 104 to the monitoring system 106. The database of pre-existing surgical object identifier data 126 is queried to match the second set of image data to the pre-existing surgical object identifier data to produce at least one of the surgical object exit count 132 and the surgical object type exit count 134. At least one of the surgical object exit count 132 and the surgical object type exit count 134 is electrically transferred 460 from the monitoring system 106 to the display screen 108. At least one of the surgical object exit count 132 and the surgical object type exit count 134 is displayed in a user-perceptible manner.

The displayed surgical object entry count 128 may be compared to the displayed surgical object exit count 132 in order to account for all surgical objects 112 by number. The displayed surgical object type entry count 130 may be compared to the displayed surgical object type exit count 134 in order to account for all surgical objects 112 by type. With the surgical object 112 on the portion of the disposable cover 358, when provided, that is covering the containment surface 238 and the discardable material 118 on the portion of the disposable cover 358 that is covering the disposal recess 240, the disposable cover 358, when provided, may be removed from the containment member 238. The surgical object 112 and the discardable material 118 on the disposal cover 358 are removed from the containment member 236 concurrently with removal of the disposable cover 358 from the containment member 236.

Figure 6:
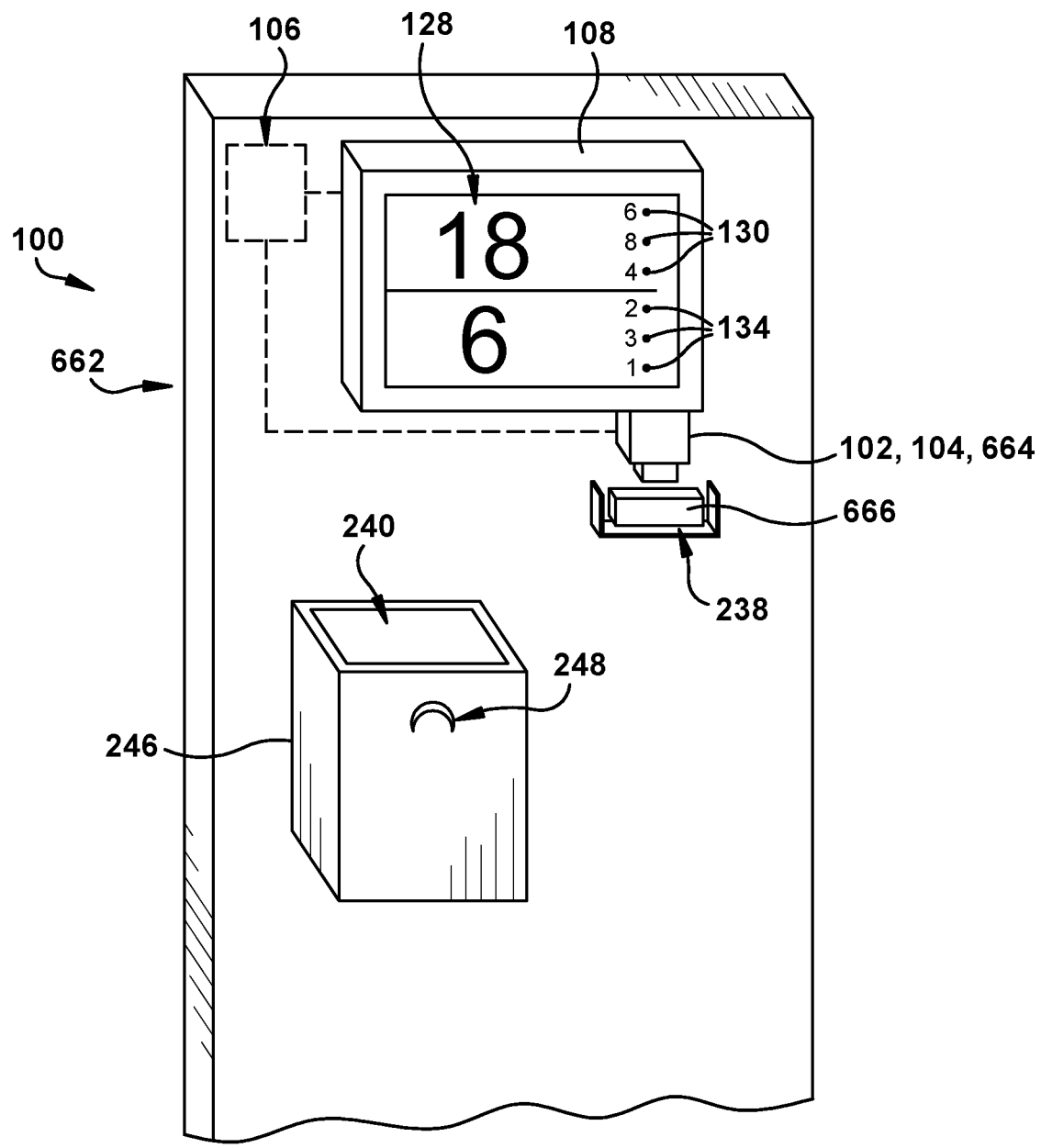
FIG. 6 is a front view of an element of the aspect of FIG. 1.

As shown in FIG. 6, at least a portion of the system for monitoring surgical objects 100 may be held in a stationary format, such as, but not limited to, via inclusion in a stationary unit 662. The term "stationary" is defined herein as fixed in position within the area of use during use of the system for monitoring surgical objects 100. The stationary unit 662 may be, but is not required to be, mounted to a wall. The stationary unit 662 may have at least one of the entry scanner 102, the exit scanner 104, the monitoring system 106, the display screen 108, the containment surface 238, the disposal recess 240, the disposal container 246, the electromagnet 242, any other feature of the system for monitoring surgical objects 100 previously described, or any combination thereof. The entry and exit scanners 102, 104 may be formed as a single entry and exit scanner 664 that provides the same functionality as both the entry and exit scanners 102, 104. At least one of the entry scanner 102, the exit scanner 104, and the single entry and exit scanner 664 may be stationary on the stationary unit 662. Alternatively, only one of the entry and exit scanners 102, 104 may be stationary on the stationary unit 662 while the other of the entry and exit scanners 102, 104 may be a handheld device. The containment surface 238 may be positioned longitudinally below at least one of the entry scanner 102, the exit scanner 104, and the single entry and exit scanner 664 so that at least one of the entry scanner 102, the exit scanner 104, and the single entry and exit scanner 664 is capable of capturing at least one of the first set of image data and the second set of image data from a surgical object identifier 110 on the containment surface 238.

As shown in FIGS. 6-11, the system for monitoring surgical objects 100 may include at least one containment box 666 having a containment box lower surface 768. The containment box lower surface 768 is configured to receive at least one surgical object 1122. At least one surgical object 112 may be positioned on the containment box lower surface 768 prior to at least a portion of a medical procedure and then the first set of image data may be captured by the entry scanner 102 and/or the single entry and exit scanner 664, as described above. Instead, or additionally, at least one surgical object 112 may be placed on the containment box lower surface 768 after and/or during at least a portion of a medical procedure and then the second set of image data may be captured by the exit scanner 104 and/or the single entry and exit scanner 664, as described above.

Figure 7:
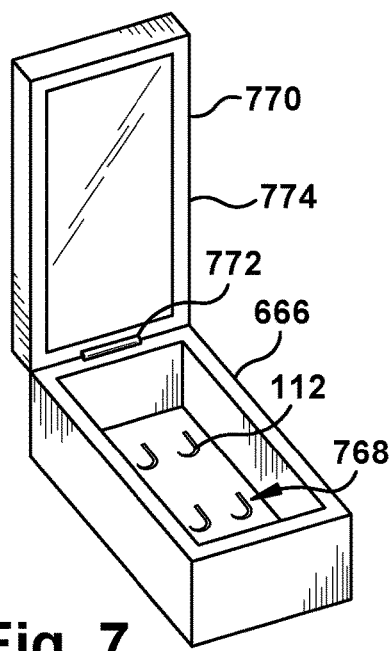
FIG. 7 is a front view of an element of the aspect of FIG. 1.

As shown in FIG. 7, the containment box 666 may have a selectively closable lid 770 that may be selectively closed over the containment box 666 to selectively restrict any surgical objects 112 that are disposed in the containment box 666 from egressing from the containment box 666. The lid 770 may be attached to the containment box 666 at a hinge 772 which allows a user to open and close the containment box 666 by rotating the lid 770 about the hinge 772. The lid 770 may have a transparent window 774. At least one of the entry scanner 102, the exit scanner 104, and the single entry and exit scanner 664 is configured to capture at least one of the first and second sets of image data from the surgical object identifier 110 through the transparent window 774 when the lid 770 having the transparent window 774 is selectively closed over the containment box 666 containing at least one surgical object 112 therein.

Figure 8:
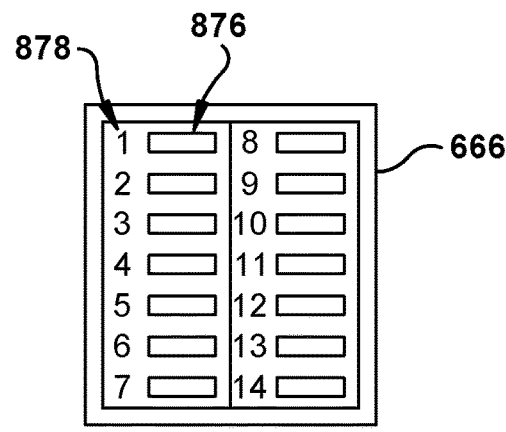
FIG. 8 is a top view of an element of the aspect of FIG. 1.

In some use environments, as shown in FIG. 8, the containment box lower surface 768 may have at least one surgical object recess 876 that is dimensioned to receive and at least partially selectively restrict a surgical object 112 that is at least partially disposed therein. The containment box lower surface 768 may have at least one numerical indicator 878 located adjacent to each surgical object recess 876 which allows at least one of a user, the entry scanner 102, the exit scanner 104, and the single entry and exit scanner 664 to identify the number of surgical objects 112 that are disposed in the surgical object recesses 876 of the containment box 666.

Figure 9:
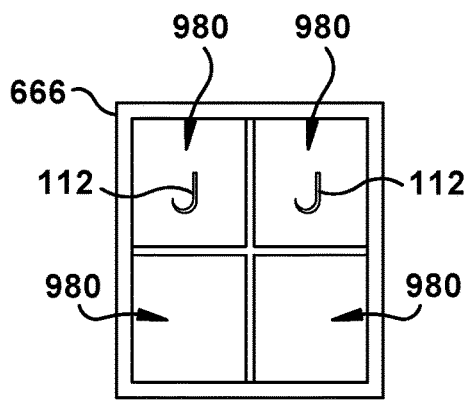
FIG. 9 is a top view of an element of the aspect of FIG. 1.
Figure 10:
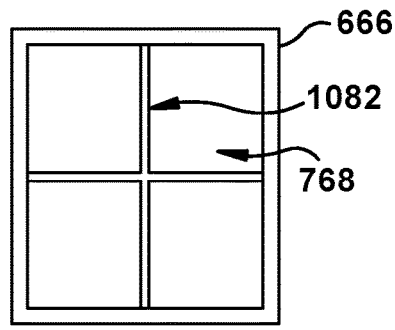
FIG. 10 is a top view of an element of the aspect of FIG. 1.
Figure 11:
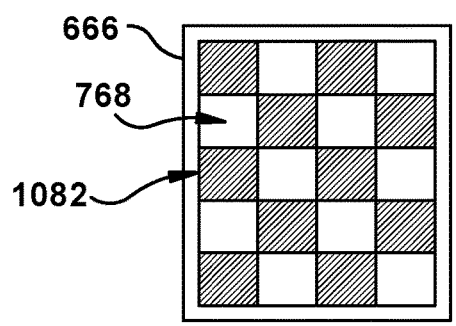
FIG. 11 is a top view of an element of the aspect of FIG. 1.

In some use environments, as shown in FIG. 9, the containment box 666 may have separate containment compartments 980 for holding surgical objects 112, and/or for holding separate types of surgical objects 112 each within separate containment compartments 980. In some use environments, as shown in FIGS. 10-11, the containment box lower surface 768 may have a spatial pattern 1082 that functions as a backdrop for at least one of the entry scanner 102, the exit scanner 104, and the single entry and exit scanner 664 so that at least one of the entry scanner 102, the exit scanner 104, and the single entry and exit scanner 664 may more readily identify at least one surgical object identifier 110 of at least one surgical object 112 that is disposed on the containment box lower surface 768. Although certain features of the containment box 666 have been shown separately in FIGS. 7-11, it should be understood that any of the features of the containment box 666 shown in any of the FIGS. 7-11 may be included in any other containment box 666 shown in FIGS. 7-11.

The containment box 666 may be used in conjunction with at least one of the entry scanner 102, the exit scanner 104, the single entry and exit scanner 664, the containment member 236, the containment surface 236, the disposal recess 240, the disposal container 246, and the stationary unit 662, any other feature previously disclosed, or any combination thereof. For example, the following description describes the use of the containment box 666 in conjunction with the entry scanner 102, the exit scanner 104, and the containment member 236. Prior to at least a portion of a medical procedure, at least one surgical object 112 may be placed in an open containment box 666. The containment box 666 is open when the lid 770 is not selectively closed over the containment box 666. The entry scanner 102 may capture the first set of data, as previously described, from the at least one surgical object 112 contained in the containment box 666. If the containment box 666 has a lid 770 with a transparent window 774, the lid 770 of the containment box 666 may be selectively closed over the containment box 666 and the entry scanner 102 may capture the first set of image data from at least one subject object identifier 110 of the at least one surgical object 112 through the transparent window 774.

Following and/or during at least a portion of the medical procedure, any surgical objects 112 that were used during the medical procedure may be placed back in the containment box 666 with the unused surgical objects 112, when present, and/or may be placed in a separate containment box 666 from that holding the unused surgical objects 112. The containment boxes 666 containing used and/or unused surgical objects 112 may be placed on the containment surface 238 of the containment member 236 and then the exit scanner 104 may capture the second set of image data in a similar manner as previously described. If the containment box 666 has a lid 770 with a transparent window 774, the lid 770 of the containment box 666 may be selectively closed over the containment box 666 and the entry scanner 102 may capture the second set of image data from at least one subject object identifier 110 of the at least one surgical object 112 through the transparent window 774. After the second set of image data is captured by the exit scanner 104, the at least one containment box 666 may be placed in at least one of the disposal recess 240 and the disposal container 246.

The following description describes the use of the containment box 666 in conjunction with the stationary unit 662 having a single entry and exit scanner 664, a containment surface 238, a disposal recess 240, and a disposal container 246. Prior to at least a portion of a medical procedure, at least one surgical object 112 may be placed in the open containment box 666. The containment box 666 containing the at least one surgical object 112 may be placed on the containment surface 238 (FIG. 7). The single entry and exit scanner 664 may capture the first set of data, as previously described, from the at least one surgical object 112 contained in the containment box 666. If the containment box 666 has a lid 770 with a transparent window 774, the lid 770 of the containment box 666 may be selectively closed over the containment box 666 and the single entry and exit scanner 664 may capture the first set of image data from at least one subject object identifier 110 of the at least one surgical object 112 through the transparent window 774. Following and/or during at least a portion of the medical procedure, any surgical objects 112 that were used during the medical procedure may be placed back in the containment box 666 with the unused surgical objects 112, when present, and/or may be placed in a separate containment box 666. The at least one containment box 666 containing used and/or unused surgical objects 112 may be placed on the containment surface 238 of the stationary unit 662 and then the single entry and exit scanner 664 may capture the second set of image data in a similar manner as previously described. If the at least one containment box 666 has a lid 770 with a transparent window 774, the lid 770 of the containment box 666 may be selectively closed over the at least one containment box 666 and the single entry and exit scanner 664 may capture the second set of image data from at least one subject object identifier 110 of the at least one surgical object 112 through the transparent window 774. After the second set of image data is captured by the single entry and exit scanner 664, the at least one containment box 666 may be placed in at least one of the disposal recess 240 and the disposal container 246.

It is contemplated that at least one of the surgical object entry count, the surgical object type entry count, the surgical object exit count, and the surgical object type exit count may be produced by a user counting the surgical objects in any appropriate manner and inputting at least one of those counts into an electronic database, a written database, the monitoring system, or any combination thereof. The user may auditorily or visually tally the surgical objects to create at least one of the surgical object entry count, the surgical object type entry count, the surgical object exit count, and the surgical object type exit count.

It is contemplated that at least one of the disposal container 246 and the containment box 666 may be selectively closed (and optionally sealed) to prevent any surgical objects 112 and/or discardable material 118 disposed therein from egressing therefrom. The selectively sealable disposal container 246 and/or containment box 666 may be selectively opened (and optionally unsealed) in order to access any surgical objects 112 and/or discardable material 118 disposed therein. For example, after a second set of image data is captured from at least one surgical object identifier 110 of at least one surgical object 112, the at least one surgical object 112 may be disposed in the disposal container 246. Once the at least one surgical object 112 is disposed in the disposal container 246, the disposal container 246 may be closed to prevent the at least one surgical object 112 from egressing from the disposal container 246. In order to verify and/or correct at least one of the surgical object entry count 128, the surgical object type entry count 130, the surgical object exit count 132, and the surgical object type exit count 134, a user may open the disposal container 246 and manually count the number of surgical objects 112, and/or the number of each type of surgical objects 112 disposed therein.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically named, but one of ordinary skill in the art will realize, based upon the components that were named, the element names which should be associated with the unnamed components; no differentiation between similar components is intended or implied solely by the presence or absence of an element names in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A system for monitoring surgical objects, comprising:
   an entry scanner that captures a first set of image data from a surgical object identifier;
   a containment member having a containment surface and an electromagnet positioned longitudinally below at least a portion of the containment surface, the containment surface defining a target field of view, the electromagnet being capable of being selectively transitioned between an off position and an on position, the electromagnet in the on position producing a magnetic field to hold the surgical object to at least a portion of the containment surface, and the electromagnetic in the off position not producing a magnetic field;
   an exit scanner that captures a second set of image data from a surgical object identifier within the target field of view;
   a monitoring system being electrically connected the entry scanner and the exit scanner, the monitoring system having a surgical object recognition module, the surgical object recognition module having
   a processor, and
   a database of pre-existing surgical object identifier data,
   the surgical object recognition module identifying at least one of the number of surgical objects, the type of surgical objects, and the number of each type of surgical objects from the first set of image data by comparing the first set of image data with the pre-existing surgical object identifier data to produce at least one of a surgical object entry count and a surgical object type entry count, the surgical object recognition module identifying at least one of the number of surgical objects, the type of surgical objects, and the number of each type of surgical objects from the second set of image data by comparing the second set of image data with the pre-existing surgical object identifier data to produce at least one of a surgical object exit count and a surgical object exit type count,
   the surgical object entry count being a numerical representation of the number of surgical objects identified by the monitoring system from the first set of image data, the surgical object type entry count being a separate numerical representation of the number of each separate type of surgical objects identified by the monitoring system from the first set of image data, the surgical object exit count being a numerical representation of the number of surgical objects identified by the monitoring system from the second set of image data, the surgical object type exit count being a separate numerical representation of the number of each separate type of surgical objects identified by the monitoring system from the second set of image data; and
   a display screen, the display screen being electrically connected to the monitoring system, the display screen displaying, in a user-perceptible format, at least one of the surgical object entry count, the surgical object exit count, the surgical object type entry count, the surgical object type exit count, the difference between the surgical object entry count and the surgical object exit count, and the difference between the surgical object type entry count and the surgical object type exit count.

2. The system of claim 1, wherein the containment member further has a disposal recess, and a disposal container longitudinally extending downward from the disposal recess.

3. The system of claim 2, including a selectively removable disposable cover, the disposable cover being configured to concurrently cover at least a portion of the containment surface and at least a portion of the disposal recess.

4. The system of claim 1, wherein the electromagnet has a surgical object detection member, the surgical object detection member being configured to detect when at least one surgical object is located on at least a portion of the containment surface, wherein when the surgical object detection member detects at least one surgical object on at least a portion of the containment surface, the surgical object detection member transitions the electromagnet to the on position.

5. The system of claim 2, wherein the containment member has a discardable material cutter, the discardable material cutter being configured to cut a discardable material attached to a surgical object.

6. The system of claim 1, wherein the surgical object identifier is a label on a surgical object package readable by at least one of the entry and exit scanners, the label containing data pertaining to at least one of the total number of surgical objects within the package, the types of each surgical object within the package, and the number of each type of surgical objects within the package.

7. The system of claim 1, wherein the surgical object identifier is at least one physical characteristic of a surgical object, the physical characteristic being at least one of the shape of the surgical object, the size of the surgical object, the weight of the surgical object, the color of the surgical object, and the outline of the surgical object.

8. The system of claim 7, including at least one containment box having a containment box lower surface and a selectively closable lid, the containment box lower surface being configured to receive at least one surgical object, the lid having a transparent window, at least one of the entry and exit scanners capturing at least one of the first and second sets of image data from the surgical object identifier through the transparent window when the lid having the transparent window is selectively closed over the containment box containing at least one surgical object therein.

9. The system of claim 1, wherein at least one of the entry scanner and exit scanner is a handheld device.

10. The system of claim 1, wherein at least one of the entry scanner, the exit scanner, the monitoring system, the display screen, and the containment surface is provided in a stationary unit.

11. The system of claim 10, including at least one containment box having a containment box lower surface and a selectively closable lid, the containment box lower surface being configured to receive at least one surgical object, the lid having a transparent window, at least one of the entry and exit scanners capturing at least one of the first and second sets of image data from the surgical object identifier through the transparent window when the lid having the transparent window is selectively closed over the containment box containing at least one surgical object therein, the entry and exit scanners being formed as a stationary single entry and exit scanner, the containment surface being positioned longitudinally below the single entry and exit scanner so that the single entry and exit scanner is capable of capturing at least one of the first set of image data and the second set of image data from the surgical object identifier on the containment surface.

12. A method for monitoring surgical objects, the method comprising:
  providing a system for monitoring surgical objects having
    an entry scanner that captures a first set of image data from a surgical object identifier,
    a containment member having a containment surface and an electromagnet positioned longitudinally below at least a portion of the containment surface, the electromagnet being capable of being selectively transitioned between an off position and an on position, the electromagnet in the on position producing a magnetic field to hold the surgical object to at least a portion of the containment surface, and the electromagnetic in the off position not producing a magnetic field,
    an exit scanner that captures a second set of image data from a surgical object identifier within a target field of view on the containment surface,
    a monitoring system being electrically connected to the entry scanner and the exit scanner, the monitoring system having a surgical object recognition module, the surgical object recognition module having
      a processor, and
      a database of pre-existing surgical object identifier data,
      the surgical object recognition module identifying at least one of the number of surgical objects, the type of surgical objects, and the number of each type of surgical objects from at least one of the first set of image data and the second set of image data, and
    a display screen, the display screen being electrically connected to the monitoring system;
  capturing a first set of image data from a surgical object identifier with the entry scanner;
  electrically transferring the first set of image data from the entry scanner to the monitoring system;
  querying the database of pre-existing surgical object identifier data to match the first set of image data to the pre-existing surgical object identifier data to produce at least one of a surgical object entry count and a surgical object type entry count, the surgical object entry count being a numerical representation of the number of surgical objects identified by the monitoring system from the first set of image data, the surgical object type entry count being a separate numerical representation of the number of each separate type of surgical objects identified by the monitoring system from the first set of image data;
  electrically transferring at least one of the surgical object entry count and the surgical object type entry count from the monitoring system to the display screen;
  displaying at least one of the surgical object entry count and the surgical object type entry count in a user-perceptible manner;
  placing the surgical object on the containment surface;
  with the surgical object on the containment surface, moving the electromagnet into the on position to selectively restrict the surgical object to the containment surface by utilizing the magnetic force of the electromagnet;
  with the surgical object restricted to the containment surface, capturing a second set of image data from the surgical object identifier with the exit scanner;
  electrically transferring the second set of image data from the exit scanner to the monitoring system;
  querying the database of pre-existing surgical object identifier data to match the second set of image data to the pre-existing surgical object identifier data to produce at least one of a surgical object exit count and a surgical object type exit count, the surgical object exit count being a numerical representation of the number of surgical objects identified by the monitoring system from the second set of image data, the surgical object type exit count being a separate numerical representation of the number of each separate type of surgical objects identified by the monitoring system from the second set of image data;
  electrically transferring at least one of the surgical object exit count and the surgical object type exit count from the monitoring system to the display screen;
  displaying at least one of the surgical object exit count and the surgical object type exit count in a user-perceptible manner;
  comparing at least one of the displayed surgical object entry count and the displayed surgical object type entry count to at least one of the displayed surgical object exit count and the displayed surgical object type exit count; and
  moving the electromagnet into the off position to remove the magnetic force selectively restricting the surgical object.

13. The method of claim 12, including:
  providing a disposal recess of the containment member;
  providing a removable disposable cover, the disposable cover being configured to concurrently cover at least a portion of the containment surface and at least a portion of the disposal recess;
  placing the disposable cover on at least a portion of the containment surface and at least a portion of the disposal recess;
  placing the surgical object on a portion of the disposable cover that is covering the containment surface;
  with the surgical object on a portion of the disposable cover that is covering the containment surface, selectively restricting the surgical object to the portion of the disposable cover that is covering the containment surface with the electromagnet;
  discarding any discardable material into the disposal recess and onto the portion of the disposable cover that is covering the disposal recess; and
  with the surgical object on a portion of the disposable cover that is covering the containment surface and the discardable material on a portion of the disposable cover that is covering the disposal recess, removing the disposable cover from the containment member;
  the surgical object and the discardable material on the disposal cover being removed from the containment member concurrently with removal of the disposable cover from the containment member.

14. The method of claim 12, including providing a label on a surgical object package readable by at least one of the entry and exit scanners as the surgical object identifier, the label containing data pertaining to at least one of the total number of surgical objects within the package, the types of each surgical object within the package, and the number of each type of surgical objects within the package.

15. The method of claim 12, including providing at least one physical characteristic of a surgical object as the surgical object identifier, the physical characteristic being at least one of the shape of the surgical object, the size of the surgical object, the weight of the surgical object, the color of the surgical object, and the outline of the surgical object.

16. The method of claim 15, wherein the entry and exit scanners are formed as a stationary single entry and exit scanner, the single entry and exit scanner, the display screen, and the containment surface are provided in a stationary unit, wherein the containment surface is positioned longitudinally below the single entry and exit scanner so that the single entry and exit scanner is capable of capturing at least one of the first set of image data and the second set of image data from the surgical object identifier of the surgical object on the containment surface, the method further including:

providing a containment box having a containment box lower surface and a selectively closable lid, the containment box lower surface being configured to receive at least one surgical object, the lid having a transparent window;

placing at least one surgical object in an open containment box;

with the subject object in the containment box, selectively closing the lid over the containment box;

placing the containment box on the containment surface; and capturing at least one of the first set of image data and the second set of image data from the surgical object identifier of the surgical object through the transparent window.

17. The method of claim 12, wherein the containment member further includes a disposal recess and a discardable material cutter, the discardable material cutter being configured to cut the discardable material attached to the surgical object, the method further including:

detaching the discardable material from the surgical object by cutting the discardable material with the discardable material cutter; and discarding any discardable material into the disposal recess.

18. The method of claim 12, wherein the monitoring system is electrically connected to at least one external system, the external system being at least one of a billing system, a patient record system, and a digital log system, the method further including:

electrically transferring at least one of the first set of image data, the second set of image data, the surgical object entry count, the surgical object exit count, the surgical object type entry count, and the surgical object type exit count from the monitoring system to the at least one external system.

* * * * *